(12) United States Patent
Kadowaki et al.

(10) Patent No.: US 6,214,843 B1
(45) Date of Patent: Apr. 10, 2001

(54) PREVENTIVES AND REMEDIES FOR ISCHEMIC INTESTINAL LESION AND ILEUS

(75) Inventors: Makoto Kadowaki, Toyonaka; Masaaki Tomoi, Higashiosaka, both of (JP)

(73) Assignee: Fujitsawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/147,169

(22) PCT Filed: Apr. 24, 1997

(86) PCT No.: PCT/JP97/01417

§ 371 Date: Jan. 27, 1999

§ 102(e) Date: Jan. 27, 1999

(87) PCT Pub. No.: WO97/40047

PCT Pub. Date: Oct. 30, 1997

(30) Foreign Application Priority Data

Apr. 25, 1996 (JP) .................................. 8-105020

(51) Int. Cl.[7] .......................... A01N 43/40; A61K 31/445
(52) U.S. Cl. ............................................... 514/322
(58) Field of Search ............................... 514/322

(56) References Cited

FOREIGN PATENT DOCUMENTS

| 64-45385 | * | 2/1989 | (JP) . |
| 2-243689 | * | 9/1990 | (JP) . |
| 3-141222 | * | 6/1991 | (JP) . |
| 4-244084 | * | 9/1992 | (JP) . |
| 4-253978 | * | 9/1992 | (JP) . |
| 5-112566 | * | 5/1993 | (JP) . |
| 6-192092 | * | 7/1994 | (JP) . |
| 7-33769 | * | 2/1995 | (JP) . |
| WO 95/18128 | * | 7/1995 | (JP) . |
| 8-12673 | * | 1/1996 | (JP) . |
| 8-500338 | * | 1/1996 | (JP) . |
| 8-99976 | * | 4/1996 | (JP) . |
| WO 95/18128 | * | 7/1995 | (WO) . |

OTHER PUBLICATIONS

Abstract to JP 3–141222 possessing a publication date of Jun. 17, 1991.*

* cited by examiner

*Primary Examiner*—Dwayne C. Jones
(74) *Attorney, Agent, or Firm*—Oblon, Spivak, McClelland, Maier & Neustadt, P.C.

(57) ABSTRACT

The present invention relates to a prophylactic and/or therapeutic composition for ischemic intestinal lesions and/or ileus which comprises as an active ingredient a pyrazolopyridine compound of the following formula:

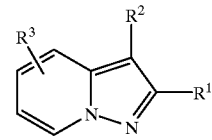

[wherein $R^1$ is lower alkyl group, etc; $R^2$ is a group of the formula:

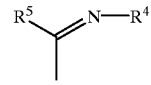

(wherein $R^4$ is protected amino group, etc; $R^5$ is hydrogen, etc); etc, and $R^3$ is hydrogen, etc]
or a salt thereof.

8 Claims, No Drawings

PREVENTIVES AND REMEDIES FOR ISCHEMIC INTESTINAL LESION AND ILEUS

This application is a 371 of PCT/JP97/01417 which was filed on Apr. 24, 1997.

TECHNICAL FIELD

The present invention relates to a pharmaceutical composition for the prophylaxis and/or therapy of ischemic intestinal lesions and/or ileus which comprises an adenosine antagonist compound or a salt thereof as an active ingredient and is useful in the pharmaceutical field.

BACKGROUND ART

Not heretofore known is an effective drug for the prevention and treatment of ischemic intestinal lesions and ileus.

DISCLOSURE OF INVENTION

While, in the field of medical care, there is a constant demand for an effective prophylactic or therapeutic drug for ischemic intestinal lesions and ileus, the present invention has for its object to meet this demand.

The inventors of the present invention discovered for the first time that a pyrazolopyridine compound, which is an adenosine antagonist, is effective in the prevention and/or treatment of ischemic intestinal lesions and ileus and have accordingly developed the present invention. The present invention, therefore, provides a pharmaceutical composition comprising said adenosine antagonist compound or salt as an active ingredient to thereby meet the above-mentioned demand.

The pharmaceutical composition of the present invention is implemented by producing a composition comprising a certain adenosine-antagonizing pyrazolopyridine compound or a salt thereof as an active ingredient, which composition is adapted for the prevention or/and treatment of ischemic intestinal lesions and/or ileus, and administering it to a man or animal.

The pyrazolopyridine compound to be used in accordance with the present invention includes pyrazolopyridine compounds of the following general formula (I) or their salts.

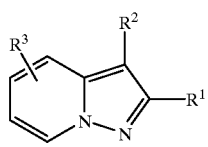

(I)

[wherein $R^1$ is lower alkyl, aryl which may have one or more suitable substituent(s), or heterocyclic group;

$R^2$ is a group of the formula:

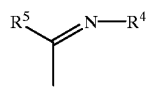

(wherein $R^4$ is protected amino or hydroxy and $R^5$ is hydrogen or lower alkyl):
cyano;
a group of the formula: —A—$R^6$
(wherein $R^6$ is acyl and A is a lower aliphatic hydrocarbon group which may have one or more suitable substituent(s));
amidated carboxy;
unsaturated heterocyclic group which may have one or more suitable substituents;
amino; or
protected amino; and
$R^3$ is hydrogen, lower alkyl, lower alkoxy, or halogen]

As examples of said pyrazolopyridine compound (I) there can be mentioned those known compounds which are disclosed in Japanese Kokai Tokkyo Koho S64-45385, Kokai Tokkyo Koho H2-243689, Kokai Tokkyo Koho H4-253978, Kokai Tokkyo Koho H5-112566, and WO 95/18128.

The salt of pyrazolopyridine compound (I) preferred for purposes of the present invention is a pharmaceutically acceptable conventional salt and as such includes but is not limited to metal salts such as salts with alkali metals, e.g. sodium salt, potassium salt, etc., and salts with alkaline earth metals, e.g. calcium salt, magnesium salt, etc., ammonium salt, salts with organic bases, e.g. trimethylamine salt, triethylamine salt, pyridine salt, picoline salt, dicyclohexylamine salt, N,N'-dibenzylethylenediamine salt, etc., salts with organic acids, e.g. acetate, trifluoroacetate, maleate, tartrate, fumarate, methanesulfonate, benzenesulfonate, formate, toluenesulfonate, etc., salts with inorganic acids, e.g. hydrochloride, hydrobromide, hydroiodide, sulfate, phosphate, etc., and salts with amino acids such as arginine, aspartic acid, glutamic acid, etc.

The preferred examples as well as definitions of the various terms used in the above and following disclosure in this specification are set forth in detail below.

The term "lower", unless otherwise indicated, means 1 through 6 carbon atom(s).

The term "higher", unless otherwise indicated, means 7 through 20 carbon atom(s).

The preferred species of "lower aliphatic hydrocarbon group" includes the lower alkyl, lower alkenyl, and lower alkynyl groups mentioned hereinafter.

The preferred species of "lower alkyl" includes straight-chain or branched alkyl groups such as methyl, ethyl, propyl, isopropyl, butyl, tert-butyl, pentyl, and hexyl. Among them, the more preferred are ($C_1$–$C_4$)alkyl groups and the still more preferred are methyl, ethyl, propyl, and isopropyl.

The preferred species of "lower alkenyl" includes straight-chain or branched alkenyl groups such as vinyl, 1-methylvinyl, 2-methylvinyl, 1-propenyl, 2-propenyl, 1-butenyl, 2-methyl-1-propenyl, 1,3-butadienyl, 1-pentenyl, 4-pentenyl, 1-hexenyl, 1,4-hexadienyl, and 5-hexenyl. Among them, the more preferred are ($C_2$–$C_4$) alkenyl groups and the still more preferred are vinyl, 1-methylvinyl, 2-methylvinyl, and 1,3-butadienyl.

The preferred species of "lower alkynyl" includes straight-chain or branched alkynyl groups such as ethynyl, 1-propynyl, 1-methylethynyl, 2-butynyl, 2-methyl-3-butynyl, 2-pentynyl, and 1-hexynyl. Among them, the preferred are ($C_2$–$C_4$)alkynyl groups and the still more preferred is ethynyl.

The "lower aliphatic hydrocarbon group" mentioned above may have one or more, preferably 1~3, suitable substituents such as halogen, e.g. chloro, bromo, fluoro and iodo.

The preferred species of "protected amino" includes groups available upon protection of amino with conventional amino-protecting groups, e.g. lower alkylamino groups such as methylamino, ethylamino, propylamino, butylamino, tert-butylamino, pentylamino, hexylamino, etc., di(lower)alkylamino groups such as dimethylamino, diethylamino, N-ethylpropylamino, dibutylamino, N-(tert-butyl)pentylamino, dihexylamino, etc., and acylamino groups which are mentioned below.

The preferred species of "acylamino" includes ureido; lower alkanoylamino such as formylamino, acetylamino, propionylamino, butyrylamino, iso-butyrylamino, pivaloylamino, hexanoylamino, etc.; lower alkoxycarbonylamino such as methoxycarbonylamino, ethoxycarbonylamino, propoxycarbonylamino, tert-butoxycarbonylamino, pentyloxycarbonylamino, hexyloxycarbonylamino, etc.; lower alkoxycarbonyl-(lower)alkanoylamino such as methoxycarbonylacetylamino, ethoxycarbonylacetylamino, 2-(propoxycarbonyl)propionylamino, 4-(tert-butoxycarbonyl)butyrylamino, 2-(butoxycarbonylmethyl)propionylamino, 2-methyl-2-(pentyloxycarbonylmethyl)propionylamino, 6-hexyloxycarbonylhexanoylamino, etc.; and lower alkanesulfonylamino such as methanesulfonylamino, ethanesulfonylamino, propanesulfonylamino, butanesulfonylamino, tert-butanesulfonylamino, pentanesulfonylamino, hexanesulfonylamino, etc.

The "lower alkanoylamino" mentioned above may have suitable substituents such as di(lower)alkylamino, e.g. dimethylamino, N-methyl-N-ethylamino, dipropylamino, di-tert-butylamino, N-pentyl-N-hexylamino, etc. and cycloamino, e.g. piperidino, which may have lower alkyl. The preferred species of such "lower alkanoylamino having suitable substituents" includes but is not limited to lower alkanoylamino groups having di(lower)alkylamino, e.g. dimethylaminocarbonylamino, 2-dimethylaminoacetylamino, 2-(N-methyl-N-ethylamino)acetylamino, 2-dimethylaminopropionylamino, 3-dipropylaminobutyrylamino, 2-(di-tert-butyl-amino)-2-methylpropionylamino, 2-dimethylamino- methyl-2-methylpropionylamino, 6-(N-pentyl-N-hexylamino)hexanoylamino, etc. and lower alkanoylamino groups having cycloamino optionally having lower alkyl, e.g. piperidinocarbonylamino, 2-piperidinoacetylamino, 2-(2-methylpiperidino)acetylamino, 2-(2-ethylpiperidino)acetylamino, 2-piperidinopropionylamino, 3-(2-ethylpiperidino)butyrylamino, 2-(4-ethylpiperidino)-2-methylpropionylamino, 2-piperidinomethyl-2-methylpropionylamino, 6-(3-propylpiperidino)hexanoylamino, etc.

The preferred species of said "acylamino" includes ureido, ($C_1$–$C_4$)alkanoylamino, ($C_1$–$C_4$)alkoxycarbonyl ($C_1$–$C_4$)alkanoylamino, di($C_1$–$C_4$)alkylamino($C_1$–$C_4$)alkanoylamino, ($C_1$–$C_4$)alkylpiperidino($C_1$–$C_4$)alkanoylamino, ($C_1$–$C_4$)alkoxycarbonylamino, ($C_1$–$C_4$)alkanesulfonylamino, ($C_1$–$C_4$)alkylamino, and di($C_1$–$C_4$)alkylamino. Among them, the still more preferred are ureido, acetylamino, 2-(ethoxycarbonyl)acetylamino, 2-dimethylaminoacetylamino, 2-(2-ethylpiperidino)acetylamino, methoxycarbonylamino, methanesulfonylamino, methylamino, and dimethylamino.

The preferred species of "acyl" includes lower alkanoyl groups such as formyl, acetyl, propionyl, butyryl, isobutyryl, pivaloyl, hexanoyl, etc.; carboxy; and protected carboxy.

The preferred examples of said "protected carboxy" include estierified carboxy, the preferred species of. which are lower alkoxycarbonyl groups, such as methoxycarbonyl, ethoxycarbonyl, propoxycarbonyl, butoxycarbonyl, tert-butoxycarbonyl, pentyloxycarbonyl hexyloxycarbonyl, etc., which may have a nitrogen-containing heterocyclic group; and amidated carboxy, the preferred species of which includes N-(lower)alkylcarbamoyl groups such as N-methylcarbamoyl, N-ethylcarbamoyl, N-isopropylcarbamoyl, N-butylcarbamoyl, N-pentylcarbamoyl, N-hexylcarbamoyl, etc.; N-(higher)alkylcarbamoyl groups such as N-heptylcarbamoyl, N-(2-methylheptyl)carbamoyl, N-nonylcarbamoyl, N-decanylcarbamoyl, N-tricyclo[3.3.1.1$^{3,7}$]decanylcarbamoyl, N-undecanylcarbamoyl, N-(bicyclo[4.3.2.]undecanyl)carbamoyl, N-dodecanylcarbamoyl, N-tridecanylcarbamoyl, N-tetradecanylcarbamoyl, N-pentadecanylcarbamoyl, N-hexadecanylcarbamoyl, N-heptadecanylcarbamoyl, N-octadecanylcarbamoyl, N-nonadecanylcarbamoyl, N-eicosanylcarbamoyl, etc.; N,N-di (lower) alkylcarbamoyl groups such as N,N-dimethylcarbamoyl, N,N-diethylcarbamoyl, N-methyl-N-ethylcarbamoyl, N,N-dipropylcarbamoyl, N,N-di(tert-butyl)carbamoyl, N-pentyl-N-hexylcarbamoyl, etc.; N-(lower)alkyl-N-ar (lower)alkylcarbamoyl groups such as N-methyl-N-benzylcarbamoyl etc.; and groups of the formula:

—CO—R$_N$ (wherein R$_N$ is a nitrogen-containing heterocyclic group which may have one or more suitable substituents, which heterocyclic group may contain other hetero atoms, such as N, O, or S, as ring atoms).

The preferred species of "nitrogen-containing heterocyclic group" includes unsaturated 3- through 8-membered (more preferably 5-~7-membered) monocyclic hetero groups containing 1 to 4 nitrogen atoms, such as azepinyl, e.g. 1H-azepinyl, pyrrolyl, pyrrolinyl, imidazolyl, pyrazolyl, pyridyl and its N-oxide, dihydropyridyl, pyrimidinyl, pyrazinyl, pyridazinyl, triazolyl, e.g. 4H-1,2,4-triazolyl, 1H-1,2,3-triazolyl, 2H-1,2,3-triazolyl, etc., tetrazolyl, e.g. 1H-tetrazolyl, 2H-tetrazolyl, etc.;

saturated 3- through 8-membered (more preferably 5-~7-membered) monocyclic hetero groups such as perhydroazepinyl, e.g. perhydro-1H-azepinyl, pyrrolidinyl, imidazolidinyl, piperidino, piperazinyl, etc.;

unsaturated fused heterocyclic groups containing 1 to 4 nitrogen atoms, such as indolyl, isoindolyl, indolizinyl, benzimidazolyl, quinolyl, isoquinolyl, indazolyl, benzotriazolyl, etc.;

saturated fused heterocyclic groups containing 1 to 4 nitrogen atoms, such as 7-azabicyclo[2.2.1]heptyl, 3-azabicyclo[3.2.2]nonanyl, etc.;

unsaturated 3- through 8-membered (more preferably 5- or 6-membered) monocyclic hetero groups containing 1 or 2 oxygen atoms and 1 to 3 nitrogen atoms, such as oxazolyl, isoxazolyl, oxadiazolyl, e.g. 1,2,4-oxadiazolyl, 1,3,4-oxadiazolyl, and 1,2,5 -oxadiazolyl, etc.;

saturated 3- through 8-membered (more preferably 5- or 6-membered) monocyclic hetero groups containing 1 or 2 oxygen atoms and 1 to 3 nitrogen atoms, such as morpholinyl, sydnonyl, etc.;

unsaturated fused heterocyclic groups containing 1 or 2 oxygen atoms and 1 to 3 nitrogen atoms, such as benzoxazolyl, benzoxadiazolyl, etc,;

unsaturated 3- through 8-membered (more preferably 5- or 6-membered) monocyclic hetero groups containing 1 or 2 sulfur atoms and 1 to 3 nitrogen atoms, such as thiazolyl, isothiazolyl, thiadiazolyl, e.g. 1,2,3-thiadiazolyl, 1,2,4-thiadiazolyl, 1,3,4-thiadiazolyl and 1,2,5-thiadiazolyl, dihydrothiazinyl, etc.;

saturated 3- through 8-membered (more preferably 5- or 6-membered) monocyclic hetero groups containing 1 or 2 sulfur atoms and 1 to 3 nitrogen atoms, such as thiazolidinyl etc.; and saturated or unsaturated monocyclic or polycyclic hetero groups, such as unsaturated fused heterocyclic groups containing 1 or 2 sulfur atoms and 1 to 3 nitrogen atoms, such as benzothiazolyl, benzothiadiazolyl, and so on.

Preferred, among those groups, are saturated 3- through 8-membered monocyclic hetero groups containing 1 to 4 nitrogen atoms, saturated fused heterocyclic groups containing 1 to 4 nitrogen atoms, and saturated 3- through 8-membered monocyclic hetero groups -containing 1 or 2 oxygen atoms and 1 to 3 nitrogen atoms.

The "nitrogen-containing heterocyclic group" mentioned above may have 1 or more suitable substituents such as said alkyl; hydroxy(lower)alkyl, e.g. hydroxymethyl, 1-hydroxyethyl, 2-hydroxyethyl, 3-hydroxypropyl, 2-hydroxybutyl, 1-methyl-1-hydroxymethylethyl, 4-hydroxypentyl, 3-hydroxyhexyl, etc.; lower alkoxy(lower)alkyl, e.g. methoxymethyl, 2-methoxyethyl, 1-ethoxyethyl, 3-propoxypropyl, 2-(tert-butoxy)butyl, 5-pentyloxypentyl, 3-hexyloxyhexyl, etc.; acyloxy(lower)alkyl such as lower alkanoyloxy(lower)alkyl, e.g. acetoxymethyl, 1-acetoxyethyl, 2-acetoxyethyl, 2-propionyloxyethyl, 3-propionyloxypropyl, 2-butylyloxybutyl, 4-pivaloyloxypentyl, 6-hexanoyloxyhexyl, etc.; protected carboxy such as said lower alkoxycarbonyl; carboxy; and acyl(lower)alkyl such as lower alkanoyl(lower)alkyl (e.g. formylmethyl, 1-formylethyl, 2-acetylethyl, 2-formylpropyl, 3-propionylpropyl, 4-formylbutyl, 2-butyrylbutyl, 1-(formylmethyl)ethyl, 3-formylpentyl, 1-isobutyrylpentyl, 4-pivaloylpentyl, 2-formylhexyl, 6-hexanoylhexyl, etc.), carboxy(lower)alkyl (e.g. carboxymethyl, 1-carboxyethyl, 2-carboxypropyl, 1-(carboxymethyl)ethyl, 4-carboxybutyl, 3-carboxypentyl, 2-carboxyhexyl, etc.), and protected carboxy(lower)alkyl [preferably esterified carboxy(lower)alkyl, more preferably lower alkoxycarbonyl(lower)alkyl such as methoxycarbonylmethyl, 2-methoxycarbonylethyl, 1-ethoxycarbonylethyl, 2-propoxycarbonylpropyl, 1-(methoxycarbonylmethyl)ethyl, 4-t-butoxycarbonylbutyl, 3-pentyloxycarbonylpentyl, 2-hexyloxycarbonylhexyl, etc., and preferably amidated carboxy(lower)alkyl, more preferably carbamoyl(lower)alkyl, N-(lower)alkylcarbamoyl (lower)alkyl, e.g. N-ethylcarbamoylmethyl, N,N-di(lower)alkylcarbamoyl(lower)alkyl, e.g. N,N-diethylcarbamoylmethyl; etc.].

The preferred species of said "nitrogen- containing heterocyclic group which may have one or more suitable substituents" includes but is not limited to piperidino which may have 1 through 4 suitable substituent groups selected from the class consisting of $(C_1-C_4)$alkyl, hydroxy$(C_1-C_4)$alkyl, $(C_1-C_4)$alkoxy$(C_1-C_4)$alkyl, $(C_1-C_4)$alkanoyloxy$(C_1-C_4)$alkyl, $(C_1-C_4)$alkoxycarbonyl, carboxy, $(C_1-C_4)$alkanoyl$(C_1-C_4)$alkyl, carboxy$(C_1-C_4)$alkyl, $(C_1-C_4)$alkoxycarbonyl$(C_1-C_4)$alkyl, carbamoyl$(C_1-C_4)$alkyl, N-$(C_1-C_4)$alkylcarbamoyl-$(C_1-C_4)$alkyl, and N,N-di $(C_1-C_4)$alkylcarbamoyl$(C_1-C_4)$alkyl, for example piperidino, 2-methylpiperidino, 2-ethylpiperidino, 3-ethylpipridino, 4-ethylpiperidino, 2-propylpiperidino, 4-isopropylpiperidino, 2-butylpiperidino, 3-(tert-butyl)piperidino, 2,2,6,6-tetramethylpiperidino, 2,2-dimethyl-6,6-diethylpiperidino, 2-hydroxymethylpiperidino, 3-hydroxymethylpiperidino, 2-(1-hydroxyethyl)piperidino, 2-(2-hydroxyethyl)piperidino, 3-(2-hydroxyethyl) piperidino, 4-(2-hydroxyethyl)piperidino, 2-(3-hydroxypropyl)piperidino, 3-(2-hydroxybutyl)piperidino, 2-(1-methyl-1-hydroxymethylethyl)piperidino, 2-methoxymethylpiperidino, 2-(2-methoxyethyl)piperidino, 2-(1-ethoxyethyl)piperidino, 3-(3-propoxypropyl) piperidino, 4-{2-(tert-butoxy)butyl}-piperidino, 2-acetoxymethylpiperidino, 3-(1-acetoxyethyl)piperidino, 2-(2-acetoxyethyl)piperidino, 3-(2-propionyloxyethyl) piperidino, 4-(3-propionyloxypropyl)piperidino, 2-(2-butyryloxybutyl)piperidino, 2-methoxycarbonylpiperidino, 2-ethoxycarbonylpiperidino, 2-propoxycarbonylpiperidino, 3-butoxycarbonylpiperidino, 4-(tert-butoxycarbonyl) piperidino, 2-carboxypiperidino, 3-carboxypiperidino, 4-carboxypiperidino, 2-(2-hydroxyethyl)-3-methylpiperidino, 2-(2-hydroxyethyl), 4-carboxypiperidino, 2-formylmethylpiperidino, 2-(1-formylethyl)piperidino, 3-(2-acetylethyl)piperidino, 4-(2-formylpropyl)piperidino, 2-(3-propionylpropyl)piperidino, 2-(4-formylbutyl) piperidino, 3-(2-butyrylbutyl)piperidino, 2-[1-(formylmethyl)ethyl]piperidino, 2-carboxymethylpiperidino, 2-(1-carboxyethyl)piperidino, 3-(2-carboxypropyl)piperidino, 4-[1-(carboxymethyl)ethyl] piperidino, 2-(4-carboxybutyl)piperidino, 2-methoxycarbonylmethylpiperidino, 2-(2-methoxycarbonylethyl)piperidino, 3-(1-ethoxycarbonylethyl)piperidino, 4-(2-propoxycarbonylpropyl)piperidino, 2-[1-(methoxycarbonylmethyl)ethyl]-piperidino, 2-(4-t-butoxycarbonylbutyl)piperidino, etc.;

pyrrolidin-1-yl which may have $(C_1-C_4)$alkoxy$(C_1-C_4)$alkyl, such as pyrrolidin-1-yl, 2-methoxymethylpyrrolidin-1-yl, 2-(2-methoxyethyl) pyrrolidin-1-yl, 2-(1-ethoxyethyl)pyrrolidin-1-yl, 3-(3-propoxypropyl)pyrrolidin-1-yl, 3-[2-(tert-butoxy) butyl]pyrrolidin-1-yl, etc;

perhydroazepin-1-yl such as perhydro-1H-azepin- 1-yl etc.;

piperazin-1-yl which may have $(C_1-C_4)$alkyl, such as piperazin-1-yl, 2-methylpiperazin-1-yl, 3-methylpiperazin-1-yl, 4-methylpiperazin-1-yl, 2-ethylpiperazin-1-yl, 3-propylpiperazin-1-yl, 4-isopropylpiperazin-1-yl, 2-butylpiperazin-1-yl, 3-(tert-butyl)piperazin-1-yl, etc.;

morpholino;

7-azabicyclo[2.2.1]heptan-7-yl; and 3-azabicyclo[3.2.2]nonan-3-yl.

The most preferred species includes piperidino, 2-methylpiperidino, 2-ethylpiperidino, 3-ethylpiperidino, 4-ethylpiperidino, 2-propylpiperidino, 2,2,6,6-tetramethylpiperidino, 2-hydroxymethylpiperidino, 2-(2-hydroxyethyl)piperidino, 4-(2-hydroxyethyl)piperidino, 2-methoxymethylpiperidino, 2-(2-methoxyethyl)piperidino, 2-acetoxymethylpiperidino, 2-(2-acetoxyethyl)piperidino, 2-ethoxycarbonylpiperidino, 2-carboxypiperidino, 2-(methoxycarbonylmethyl)piperidino, 2-carboxymethylpiperidino, 2-carbamoylmethylpiperidino, 2-(N-ethylcarbamoylmethyl)piperidino, 2-N,N-diethylcarbamoylmethyl)piperidino, pyrrolidin-1-yl, 2-methoxymethylpyrrolidin-1-yl, perhydro-1H-azepin-1-yl, 4-methylpiperazin-1-yl, morpholino, 7 -azabicyclo[2.2.1] heptan-7-yl, and 3-azabicyclo-[3.2.2]nonan-3-yl.

The preferred species of "aryl" includes phenyl, naphthyl, indenyl, anthryl, etc. and this "aryl" may have one or more suitable substituents, for example halogen such as fluoro, chloro, bromo, and iodo; lower alkoxy such as methoxy, ethoxy, propoxy, tert-butoxy, pentyloxy, and hexyloxy; nitro; amino; and said protected amino.

The preferred species of such "aryl which may have one or more suitable substituents" includes phenyl which may have 1 through 3 suitable substituent groups selected from the class consisting of halogen, $(C_1-C_4)$alkoxy, nitro, amino, $(C_1-C_4)$alkanoylamino, $(C_1-C_4)$alkoxycarbonylamino, $(C_1-C_4)$alkanesulfonylamino, $(C_1-C_4)$alkylamino, and di$(C_1-C_4)$alkylamino. Among them, the preferred are phenyl, phenyl having chloro, phenyl having methoxy, phenyl having nitro, phenyl having amino, phenyl having acetylamino, phenyl having methoxycarbonylamino, phenyl having methanesulfonylamino, phenyl having methylamino, and phenyl having dimethylamino.

The preferred species of "heterocyclic group" includes not only those species mentioned for said "nitrogen-containing heterocyclic group" but also unsaturated 3- through 8-membered (more preferably 5- or 6-membered) monocyclic hetero groups containing one oxygen atom, such as furyl etc.; unsaturated 3- through 8-membered (more preferably 5-or 6-membered) monocyclic hetero groups containing one oxygen atom and 1 or 2 sulfur atoms, such as dihydrooxathiinyl etc.; unsaturated fused heterocyclic groups containing 1 or 2 sulfur atoms, such as benzothienyl, benzodithiinyl, etc.; and unsaturated fused heterocyclic groups containing one oxygen atom and 1 or 2 sulfur atoms, such as benzoxathiinyl etc. Among those groups, the preferred are unsaturated 3-through 8-membered monocyclic hetero groups containing 1 to 4 nitrogen atoms and the still more preferred is pyridyl. The most preferred includes 2-pyridyl, 3-pyridyl, and 4-pyridyl.

The preferred species of "lower alkenyl having halogen" includes 1-fluorovinyl, 1-bromovinyl, 1-chloro-2-methylvinyl, 1-bromo-1-propenyl, 2-chloro-2-propenyl, 1-iodo-1-butenyl, 1-bromo-2-methyl-1-propenyl, 3-bromo-1,3-butadienyl, 1-chloro-1-pentenyl, 4-chloro-4-pentenyl, and 1-bromo-1-hexenyl.

The preferred species of "lower alkoxy" includes methoxy, ethoxy, propoxy, isopropoxy, butoxy, tert-butoxy, pentyloxy, and hexyloxy.

The preferred species of "halogen" includes fluoro, chloro, bromo, and iodo.

The preferred species of "leaving group" includes di(lower)alkylamino such as dimethylamino, diethylamino, N-ethylpropylamino, dibutylamino, N-pentylhexylamino, etc.; said lower alkoxy; said halogen; and lower alkylthio such as methylthio, ethylthio, propylthio, butylthio, pentylthio, and hexylthio.

The preferred species of the "unsaturated heterocyclic group" of said "unsaturated heterocyclic group which may have one or more suitable substituents" includes unsaturated monocyclic or polycyclic hetero groups containing at least one hetero atom such as nitrogen, oxygen, sulfur, etc.

The preferred species of such "unsaturated heterocyclic group" thus includes unsaturated 3-through 8-membered (more preferably 5- through 7-membered) monocyclic hetero groups containing 1 to 4 nitrogen atoms such as azepinyl, e.g. 1H-azepinyl etc., pyrrolyl, pyrrolinyl, imidazolyl, pyrazolyl, pyridyl, dihydropyridyl, e.g. 1,2-dihydropyridyl, 1,4-dihydropyridyl, etc., tetrahydropyridyl, e.g. 1,2,3,6-tetrahydropyridyl etc., pyrimidinyl, dihydropyrimidinyl, e.g. 1,2-dihydropyrimidinyl etc., pyrazinyl, pyridazinyl, dihydropyridazinyl, e.g. 2,3-dihydropyridazinyl, 1,4-dihydropyridazinyl, etc., tetrahydropyridazinyl, e.g. 2,3,4,5-tetrahydropyridazinyl etc., triazolyl, e.g. 4H-1,2,4-triazolyl, 1H-1,2,3-triazolyl, 2H-1,2,3-triazolyl, etc., and tetrazolyl, e.g. 1H-tetrazolyl, 2H-tetrazolyl, etc.;

unsaturated fused heterocyclic groups containing 1 to 4 nitrogen atoms, for example indolyl, isoindolyl, indolizinyl, benzimidazolyl, quinolyl, dihydroquinolyl, e.g. 2,3-dihydroquinolyl etc., isoquinolyl, indazolyl, benzotriazolyl, etc.;

unsaturated 3-through 8-membered (more preferably 5- or 6-membered) monocyclic hetero groups containing 1 or 2 oxygen atoms and 1 to 3 nitrogen atoms, for example oxazolyl, isoxazolyl, dihydroisoxazolyl, e.g. 2,5-dihydroisoxazolyl etc., and oxadiazolyl, e.g. 1,2,4-oxadiazolyl, 1,3,4-oxadiazolyl, 1,2,5-oxadiazolyl, etc.;

unsaturated fused heterocyclic groups containing 1 or 2 oxygen atoms and 1 to 3 nitrogen atoms, for example benzoxazolyl, benzoxadiazolyl, etc.;

unsaturated 3- through 8-membered (more preferably 5- or 6-membered) monocyclic hetero groups containing 1 or 2 sulfur atoms and 1 to 3 nitrogen atoms, for example, thiazolyl, dihydrothiazolyl, e.g. 2,3-dihydrothiazolyl etc., isothiazolyl, thiadiazolyl, e.g. 1,2,3-thiadiazolyl, 1,2,4-thiadiazolyl, 1,3,4-thiadiazolyl, 1,2,5-thiadiazolyl, etc., dihydrothiazinyl, etc.;

unsaturated fused heterocyclic groups containing 1 or 2 sulfur atoms and 1 to 3 nitrogen atoms, for example, benzothiazolyl, benzothiadiazolyl, e.g. benzo[d]-[1,2,3]thiadiazolyl etc., and imidazothiadiazolyl, e.g. 5H-imidazo[2,1-b][1,3,4]thiadiazolyl, etc.;

unsaturated 3- through 8-membered (more preferably 5- or 6-membered) monocyclic hetero groups containing 1 or 2 sulfur atoms, for example thienyl, dihydrothiinyl, etc.;

unsaturated 3- through 8-membered (more preferably 5- or 6-membered) monocyclic hetero groups containing one oxygen atom, for example furyl etc.;

unsaturated 3- through 8-membered (more preferably 5- or 6-membered) monocyclic hetero groups containing one oxygen atom and 1 or 2 sulfur atoms, for example dihydrooxathiinyl etc.;

unsaturated fused heterocyclic groups containing 1 or 2 sulfur atoms, for example benzothienyl, benzodithiinyl, etc.; and unsaturated fused heterocyclic groups containing 1 oxygen atom and 1 or 2 sulfur atoms, for example benzoxathiinyl etc.

Among them, the preferred are unsaturated heterocyclic groups containing at least one nitrogen atom as the hetero atom and the more preferred are unsaturated 3- through 8-membered monocyclic hetero groups containing 1 to 4 nitrogen atoms and unsaturated fused heterocyclic groups containing 1 or 2 sulfur atoms and 1 to 3 nitrogen atoms. The still more preferred examples are pyridazinyl, dihydropyridazinyl, tetrahydropyridazinyl, pyrimidinyl, dihydropyrimidinyl, pyridyl, dihydropyridyl, tetrahydropyridyl, pyrazolyl, and imidazothiadiazolyl. The most preferred are pyridazinyl, 2,3-dihydropyridazinyl, 1,4-dihydropyridazinyl, 2,3,4,5-tetrahydropyridazinyl, pyrimidinyl, 1,2-dihydropyrimidinyl, pyridyl, 1,2-dihydropyridyl, 1,4-dihydropyridyl, 1,2,3,6-tetrahydropyridyl, pyrazolyl, and imidazo[2,1-b][1,3,4]thiadiazolyl.

The "unsaturated heterocyclic group" mentioned above may have one or more (preferably 1 to 4) suitable substituents, for example lower alkyl, e.g. methyl, ethyl, propyl, isopropyl, butyl, tert-butyl, pentyl, and hexyl, which may have 1 or more (preferably 1 to 4) suitable substituent groups such as those mentioned below; carboxy(lower)alkenyl such as 1-carboxyvinyl, 2-carboxyvinyl, 1-carboxy-2-propenyl, 3-carboxy-2-propenyl, 3-carboxy-2-butenyl, 4-carboxy-2-methyl-2-butenyl, 3-carboxy-1-hexenyl, etc.; amino; di(lower)alkylamino such as dimethylamino, N-methylethylamino, dipropylamino, N-butyl-(2-methylbutyl)amino, N-pentylhexylamino, etc.; halogen such as fluoro, chloro, bromo, and iodo; lower alkoxy such as methoxy, ethoxy, propoxy, isopropoxy, butoxy, tert-butoxy, pentyloxy, hexyloxy, etc.; oxo; hydroxy; cyano; and the acyl mentioned below.

The preferred species of "acyl" includes lower alkanoyl, for example formyl, acetyl, propionyl, butyryl, isobutyryl, pivaloyl, hexanoyl, etc., carboxy, and protected carboxy.

The preferred species of the "protected carboxy" mentioned just above includes esterified carboxy which is preferably lower alkoxycarbonyl such as methoxycarbonyl, ethoxycarbonyl, propoxycarbonyl, tert-butoxycarbonyl, pentyloxycarbonyl, and hexyloxycarbonyl and amidated carboxy which is preferably carbamoyl or N,N-di(lower) alkylcarbamoyl, the two lower alkyl groups of which may jointly form a 3- through 6-membered ring, such as N,N-dimethylcarbamoyl, N-methyl-N-ethylcarbamoyl, N,N-diethylcarbamoyl, N,N-dipropylcarbamoyl, N-butyl-N-tert-butylcarbamoyl, N,N-dipentylcarbamoyl, N-pentyl-N-hexylcarbamoyl, 1-aziridinylcarbonyl, 1-azetidinylcarbonyl, 1-pyrrolidinylcarbonyl, piperidinocarbonyl, etc.

The preferred species of "suitable substituent" of said "lower alkyl which may have 1 or more suitable substituents" includes hydroxy, said halogen, said lower alkoxy, and said acyl.

The preferred species of "lower alkyl having 1 or more suitable substituents" includes lower alkyl having hydroxy and halogen, for example 1-hydroxy-1-chloromethyl, 1-hydroxy-2-chloroethyl, 2-hydroxy-3-fluoropropyl, 2-hydroxy-3,3,3-trichloropropyl, 3-bromo-4-hydroxy-4-iodobutyl, 1-chloro-2-hydroxy-4-fluoropentyl, 3,4-dihydroxy-6-chlorohexyl, etc.;

hydroxy(lower)alkyl such as hydroxymethyl, 2-hydroxyethyl, 2-hydroxypropyl, 3-hydroxypropyl, 1-hydroxy-1-methylethyl, 1-hydroxybutyl, 1-hydroxymethyl-1-methylethyl, 3-hydroxypentyl, 2-hydroxyhexyl, etc.;

lower alkoxy(lower)alkyl such as methoxymethyl, ethoxymethyl, 2-ethoxyethyl, 1-propoxyethyl, 3-isopropoxypropyl, 2-butoxybutyl, 1-tert-butoxymethyl-1-methylethyl, 5-pentyloxypentyl, hexyloxymethyl, 3-hexyloxyhexyl, etc.;

carboxy(lower)alkyl such as carboxymethyl, 2-carboxyethyl, 2-carboxypropyl, 3-carboxypropyl, 2-carboxy-1-methylethyl, 4-carboxybutyl, 1-carboxymethyl-1-methylethyl, 3-carboxypentyl, 2-carboxyhexyl, etc.; and preferably acyl(lower)alkyl, for example protected carboxy(lower)alkyl, e.g. esterified carboxy(lower)alkyl and amidated carboxy(lower)alkyl, and more preferably lower alkoxycarbonyl (lower)alkyl such as methoxycarbonylmethyl, ethoxycarbonylmethyl, 2-methoxycarbonylethyl, 2-ethoxycarbonylethyl, 1-propoxycarbonylethyl, 3-ethoxycarbonylpropyl, 2-butoxycarbonylbutyl, 4-ethoxycarbonylbutyl, 1-tert-butoxycarbonylmethyl-1-methylethyl, 5-pentyloxycarbonylpentyl, hexyloxycarbonylmethyl, 3-hexyloxycarbonylhexyl, etc., carbamoyl(lower)alkyl such as carbamoylmethyl, 2-carbamoylethyl, 3-carbamoylpropyl, 2-carbamoyl-1-methylethyl, 4-carbamoylbutyl, 1-carbamoylmethyl-1-methylethyl, 5-carbamoylpentyl, 3-carbamoylhexyl, etc., N,N-di(lower)alkylcarbamoyl(lower)alkyl, the two lower alkyl groups on the nitrogen atom of which may jointly form a 3- through 6-membered ring, such as N,N-dimethylcarbamoylmethyl, 2-(N,N-dimethylcarbamoyl)ethyl, 2-(N-methyl-N-ethylcarbamoyl)ethyl, 3-(N-methyl-N-ethylcarbamoyl) propyl, 2-(N,N-dipropylcarbamoyl)-1-methylethyl, 4-(N,N-dipropylcarbamoyl)butyl, 1-(N,N-dimethylcarbamoyl)methyl-1-methylethyl, 5-(N-pentyl-N-hexylcarbamoyl)pentyl, 3-(N-pentyl-N-hexylcarbamoyl)hexyl, (1-aziridinylcarbonyl)methyl, 2-(1-azetidinylcarbonyl)ethyl, 2-(piperidinocarbonyl) ethyl, 3-(1-pyrrolidinylcarbonyl)propyl, 2-(piperidinocarbonyl)-1-methylethyl, 4-(1-azetidinylcarbonyl)butyl, 1-(1-aziridinylcarbonyl) methyl-1-methylethyl, 3-(1-pyrrolidinylcarbonyl) pentyl, 6-(piperidinocarbonyl)hexyl, etc.

The preferred substituent group for "unsaturated heterocyclic group" includes lower alkyl, lower alkyl having hydroxy and halogen, hydroxy(lower)alkyl, lower alkoxy (lower)alkyl, carboxy(lower)alkyl, lower alkoxycarbonyl (lower)alkyl, carbamoyl(lower)alkyl, N,N-di(lower) alkylcarbamoyl(lower)alkyl, the two lower alkyl groups on the nitrogen atom of which may jointly form a 3- through 6-membered ring, carboxy(lower)alkenyl, di(lower) alkylamino, halogen, lower alkoxy, oxo, carboxy, lower alkoxycarbonyl, lower alkanoyl, amino, cyano, and hydroxy. Among them, the still more preferred substituent groups are $(C_1-C_4)$alkyl, $(C_1-C_4)$alkyl having hydroxy and halogen, hydroxy$(C_1-C_4)$alkyl, $(C_1-C_4)$alkoxy$(C_1-C_4)$alkyl, carboxy$(C_1-C_4)$alkyl, $(C_1-C_4)$alkoxycarbonyl$(C_1-C_4)$alkyl, carbamoyl$(C_1-C_4)$alkyl, N,N-di$(C_1-C_4)$alkylcarbamoyl $(C_1-C_4)$alkyl, piperidinocarbonyl$(C_1-C_4)$alkyl, carboxy $(C_2-C_4)$alkenyl, di$(C_1-C_4)$alkylamino, halogen, $(C_1-C_4)$ alkoxy, oxo, carboxy, $(C_1-C_4)$alkoxycarbonyl, $(C_1-C_4)$ alkanoyl, amino, cyano, and hydroxy. The most preferred substituent groups are methyl, propyl, 2-hydroxy-3,3,3-trichloropropyl, 2-hydroxyethyl, 3-hydroxypropyl, 2-ethoxyethyl, 2-carboxyethyl, 3-carboxypropyl, 4-carboxybutyl, methoxycarbonylmethyl, 2-methoxycarbonylethyl, 3-ethoxycarbonylpropyl, 4-ethoxycarbonylbutyl, 2-carbamoylethyl, 2-(N,N-dimethylcarbamoyl)ethyl, 2-(piperidinocarbonyl)ethyl, 2-carboxyvinyl, dimethylamino, chloro, methoxy, oxo, carboxy, ethoxycarbonyl, methoxycarbonyl, acetyl, amino, cyano, and hydroxy.

The "unsaturated heterocyclic group" of said "unsaturated heterocyclic group which may have one or more suitable substituents" may have one or more (preferably 1 to 4) of the following substituent groups in addition to the above-mentioned substituent groups.

The substituent groups which may thus be present include amino(lower)alkyl; lower alkylamino(lower)alkyl; carboxy (lower)alkylamino(lower)alkyl; protected carboxy(lower) alkylamino(lower)alkyl; lower alkylamino(lower)alkyl having hydroxy and aryloxy; protected amino(lower)alkyl; cyano(lower)alkyl; cyano(higher)alkyl; lower alkyl having a heterocyclic group optionally having 1 or more suitable substituents; higher alkyl having a heterocyclic group optionally having 1 or more suitable substituents; ar(lower) alkyl; lower alkenyl; heterocyclyl which may have 1 or more suitable substituents; cyclo (lower)alkyl which may have 1 or more suitable substituents; or cyclo (lower) alkenyl which may have one or more suitable substituents.

The above substituent groups are now specifically explained.

The preferred species of "amino(lower)alkyl" includes aminomethyl, 1-aminoethyl, 2-aminoethyl, 2-aminopropyl, 3-aminobutyl, 2-amino-1,1-dimethylethyl, 5-aminopentyl, 1-aminohexyl, etc. Among them, the more preferred are amino($C_1$–$C_4$)alkyl, and the still more preferred is 2-aminoethyl.

The preferred species of "lower alkylamino(lower)alkyl" includes mono- or di(lower)alkylamino(lower)alkyl groups such as methylaminomethyl, 2-(ethylamino)ethyl, 3-(propylamino)propyl, 2-(propylamino)butyl, 2-(t-butylamino)-1,1-dimethylethyl, 4-pentylaminopentyl, 6-hexylaminohexyl, dimethylaminomethyl, 2-dimethylaminoethyl, 1-(N-methylethylamino)ethyl, 1-dimethylaminopropyl, 2-diethylaminopropyl, 3-dimethylaminopropyl, 3-(N-propylbutylamino)butyl, 4-dimethylaminobutyl, 2-dibutylamino-1,1-dimethylethyl, 4-dipentylaminopentyl, 6-(N-pentylhexylamino)hexyl, etc. Among them, the more preferred are di(lower)alkylamino (lower)alkyl groups and the still more preferred are di($C_1$–$C_4$)alkylamino($C_1$–$C_4$)alkyl groups. The most preferred groups are 2-dimethylaminoethyl, 3-dimethylaminopropyl, and 4-dimethylaminobutyl.

The preferred species of "carboxy(lower)alkylamino (lower)alkyl" includes carboxymethylaminomethyl, 2-(carboxymethylamino)ethyl, 2-(1-carboxyethylamino) ethyl, 3-(2-carboxypropylamino)propyl, 2-(3-carboxypropylamino)butyl, 2-(2-carboxy-1,1-dimethylethylamino)-1,1-dimethylethyl, 4-(5-carboxypentylamino)pentyl, 6-(3-carboxyhexylamino) hexyl, etc. Among them, the more preferred are carboxy ($C_1$–$C_4$)alkylamino($C_1$–$C_4$)alkyl groups and the most preferred is 2-(carboxymethylamino)ethyl.

The preferred "protected carboxy" of "protected carboxy (lower)alkylamino(lower)alkyl" includes esterified carboxy, the ester moiety of which includes but is not limited to lower alkyl esters (e.g. methyl ester, ethyl ester, propyl ester, isopropyl ester, butyl ester, isobutyl ester, t-butyl ester, pentyl ester, hexyl ester, 1-cyclopropylethyl ester, etc.) which may have suitable substituent groups, for example lower alkanoyloxy(lower)alkyl esters (e.g. acetoxymethyl ester, propionyloxymethyl ester, butyryloxymethyl ester, valeryloxymethyl ester, pivaloyloxymethyl ester, 1-acetoxyethyl ester, 1-propionyloxyethyl ester, pivaloyloxymethyl ester, 2-propionyloxyethyl ester, hexanoyloxymethyl ester, etc.), lower alkanesulfonyl(lower)alkyl esters (e.g. 2-mesylethyl ester etc.) or mono(or di or tri)halo (lower) alkyl esters (e.g. 2-iodoethyl ester, 2,2,2-trichloroethyl ester, etc.); lower alkenyl esters (e.g. vinyl ester, allyl ester, etc.); lower alkynyl esters (e.g. ethynyl ester, propynyl ester, etc.); ar(lower)alkyl esters which may have suitable substituents [e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-t-butylbenzyl ester, etc.]; aryl esters which may have suitable substituents (e.g. phenylester, 4-chlorophenyl ester, tolyl ester, 4-t-butylphenyl ester, xylyl ester, mesityl ester, cumenyl ester, etc.).

The preferred "protected carboxy(lower)alkylamino (lower)alkyl" are esterified carboxy(lower)alkylamino (lower)alkyl groups, the preferred examples of which include lower alkoxycarbonyl(lower)alkylamino(lower) alkyl, such as methoxycarbonylmethylaminomethyl, 2-(ethoxycarbonylmethylamino)ethyl, 2-(1-ethoxycarbonylethylamino)ethyl, 3-(2-propoxycarbonylpropylamino)propyl, 2-(3-butoxycarbonylpropylamino)butyl, 2-(2-t-butoxycarbonyl-1,1-dimethylethylamino)-1,1-dimethylethyl, 4-(5-pentyloxycarbonylpentylamino)pentyl, 6-(3-hexyloxycarbonylhexylamino)hexyl, etc. The still more preferred are ($C_1$–$C_4$)alkoxycarbonyl($C_1$–$C_4$)alkylamino ($C_1$–$C_4$)alkyl groups and the most preferred is 2-(ethoxycarbonylmethylamino)ethyl.

The preferred "lower alkylamino(lower)alkyl having hydroxy and aryloxy" includes said "lower alkylamino (lower) alkyl" having "hydroxy" and "aryloxy" (e.g. phenoxy, tolyloxy, naphthyloxy, etc.), the preferred species of which includes 1-(1-naphthyloxy)-1-hydroxymethylaminomethyl, 2-(1-hydroxy-2-phenoxyethylamino)ethyl, 2-[2-hydroxy-3-(1-naphthyloxy) propylamino]ethyl, 2-[4-hydroxy-3-(p-tolyloxy) butylamino]propyl, 2-[4-hydroxy-1-(2-naphthyloxy) butylamino]-1,1-dimethylethyl, 4-[1-hydroxy-5-(1-naphthyloxy)pentylamino]pentyl, 6-[2-hydroxy-4-(2-naphthyloxy)hexylamino]hexyl, etc. Among them, the more preferred is ($C_1$–$C_4$)alkylamino($C_1$–$C_4$)alkyl having hydroxy and naphthyloxy and the still more preferred is 2-[2-hydroxy-3-(1-naphthyloxy)propylamino]ethyl.

The preferred "protected amino(lower)alkyl" includes acylamino(lower)alkyl groups.

The preferred acylamino includes lower alkanoylamino (e.g. formylamino, acetylamino, propionylamino, hexanoylamino, pivaloylamino, etc.), mono (or di or tri)halo (lower)alkanoylamino (e.g. chloroacetylamino, trifluoroacetylamino, etc.), lower alkoxycarbonylamino (e.g. methoxycarbonylamino, ethoxycarbonylamino, t-butoxycarbonylamino, t-pentyloxycarbonylamino, hexyloxycarbonylamino, etc.) mono (or di or tri)halo(lower) alkoxycarbonylamino (e.g. chloromethoxycarbonylamino, dichloroethoxycarbonylamino, trichloroethoxycarbonylamino, etc.), aroylamino (e.g. benzoylamino, toluoylamino, xyloylamino, naphthoylamino, etc.), ar(lower)alkanoylamino such as phenyl(lower)alkanoylamino (e.g. phenylacetylamino, phenylpropionylamino, etc.), aryloxycarbonylamino (e.g. phenoxycarbonylamino, naphthyloxycarbonylamino, etc.), aryloxy(lower)alkanoylamino such as phenoxy(lower) alkanoylamino (e.g. phenoxyacetylamino, phenoxypropionylamino, etc.), arylglyoxyloylamino (e.g. phenylglyoxyloylamino, naphthylglyoxyloylamino, etc.), ar(lower)alkoxycarbonylamino which may have suitable substituents, such as phenyl(lower)alkoxycarbonylamino which may have nitro or lower alkoxy (e.g. benzyloxycarbonylamino, phenethyloxycarbonylamino, p-nitrobenzyloxycarbonylamino, p-methoxybenzyloxycarbonylamino, etc.), thienylacetylamino, imidazolylacetylamino, furylacetylamino, tetrazolylacetylamino, thiazolylacetylamino, thiadiazolylacetylamino, thienylpropionylamino, thiadiazolylpropionylamino, lower alkylsulfonylamino (e.g. methylsulfonylamino, ethylsulfonylamino, propylsulfonylamino, isopropylsulfonylamino, pentylsulfonylamino, butylsulfonylamino, etc.), arylsulfonylamino (e.g. phenylsulfonylamino, tolylsulfonylamino, xylylsulfonylamino, naphthylsulfonylamino, etc.), ar(lower) alkylsulfonylamino such as phenyl(lower) alkylsulfonylamino (e.g. benzylsulfonylamino, phenethylsulfonylamino, benzhydrylsulfonylamino, etc.), and imido (e.g. 1,2-cyclohexanedicarboximido, succinimide, phthalimido, etc.).

The preferred species of said "protected amino(lower) alkyl" includes imido(lower)alkyl groups such as phthalimidomethyl, 2-phthalimidoethyl, 1-(1,2-cyclohexanedicarboximido)ethyl, 2-succinimidopropyl, 3-phthalimidobutyl, 2-(1,2-cyclohexanedicarboximido)-1,1-dimethylethyl, 5-phthalimidopentyl, 1-phthalimidohexyl, etc. The more preferred are imido($C_1$–$C_4$)alkyl groups and the most preferred is 2-phthalimidoethyl.

The preferred species of "cyano(lower)alkyl", includes cyanomethyl, 1-cyanoethyl, 2-cyanoethyl, 3-cyanopropyl, 2-cyanobutyl, 4-cyanobutyl, 2-cyano-1,1-dimethylethyl, 4-cyanopentyl, 5-cyanopentyl, and 6-cyanohexyl. Among them, the more preferred are cyano($C_1$–$C_6$)alkyl groups and the most preferred are cyanomethyl, 2-cyanomethyl, 3-cyanopropyl, 4-cyanobutyl, 5-cyanopentyl, and 6-cyanohexyl.

The preferred species of "cyano(higher)alkyl" includes 7-cyanoheptyl, 8-cyanooctyl, 4-cyanooctyl, 8-cyano-3-methylheptyl, 9-cyanononyl, 1-cyanononyl, 10-cyanodecyl, 8-cyanoundecyl, 12-cyanododecyl, 11-cyano-4-methylundecyl, 13-cyanotridecyl, 6-cyanotetradecyl, 15-cyanopentadecyl, 12-cyanohexadecyl, 17-cyanoheptadecyl, 4-cyanooctadecyl, 19-cyanononadecyl, 1-cyano-12-ethylheptadecyl, 20-cyanoeicosyl, etc. Among them, the more preferred are cyano($C_7$–$C_{16}$)alkyl groups and the still more preferred are 7-cyanoheptyl, 8-cyanooctyl, 9-cyanonoyl, 10-cyanodecyl, and 12-cyanododecyl.

The preferred species of "lower alkyl" includes straight-chain or branched alkyl groups such as methyl, ethyl, propyl, isopropyl, butyl, t-butyl, pentyl, and hexyl.

The preferred species of "lower alkenyl" includes straight-chain or branched alkenyl groups such as vinyl, allyl, 2-butenyl, 2-methyl-2-propenyl, 4-pentenyl, and 3-hexenyl. Among them, the more preferred are ($C_2$–$C_4$) alkenyl groups and the still more preferred is vinyl.

The preferred species of "lower alkyl" of said "lower alkyl having a heterocyclic group optionally having 1 or more suitable substituents" includes the same groups as mentioned for the preferred "lower alkyl". The more preferred are ($C_1$–$C_6$) alkyl groups and the most preferred are methyl, ethyl, propyl, butyl, pentyl, and hexyl.

The preferred species of "higher alkyl" of said "higher alkyl having a heterocyclic group optionally having 1 or more suitable substituents" includes heptyl, octyl, 3-methylheptyl, nonyl, 2,6-dimethylheptyl, decyl, undecyl, dodecyl, 4-methyldodecyl, tridecyl, tetradecyl, pentadecyl, hexadecyl, heptadecyl, octadecyl, nonadecyl, 12-ethylheptadecyl, eicosyl, etc. Among them, ($C_7$–$C_{16}$) alkyl groups are preferred, with heptyl, octyl, nonyl, decyl, and dodecyl being particularly preferred.

The preferred "heterocyclic group" of said "lower alkyl having a heterocyclic group optionally having 1 or more suitable substituents" and of said "higher alkyl having a heterocyclic group optionally having 1 or more suitable substituents" includes saturated or unsaturated monocyclic or polycyclic hetero groups containing at least one hetero atom selected from among oxygen, sulfur, nitrogen, etc. The particularly preferred heterocyclic group includes 3- through 8-membered unsaturated monocyclic hetero groups containing 1 to 4 nitrogen atoms, for example pyrrolyl, pyrrolinyl, imidazolyl, pyrazolyl, pyridyl and its N-oxide, pyrimidyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), dihydrotriazinyl (e.g. 4,5-dihydro-1,2,4-triazinyl, 2,5-dihydro-1,2,4-triazinyl, etc.), etc.;

3- through 8-membered saturated monocyclic hetero groups containing 1 to 4 nitrogen atoms, for example pyrrolidinyl, imidazolidinyl, piperidyl (e.g. piperidino), piperazinyl, etc.;

unsaturated fused heterocyclic groups containing 1 to 5 nitrogen atoms, for example indolyl, isoindolyl, indolizinyl, benzimidazolyl, quinolyl, isoquinolyl, indazolyl, benzotriazolyl, tetrazolopyridyl, tetrazolopyridazinyl (e.g. tetrazolo[1,5-b]-pyridazinyl etc.), dihydrotriazolopyridazinyl, etc.;

3- through 8-membered unsaturated monocyclic hetero groups containing 1 or 2 oxygen atoms and 1 to 3 nitrogen atoms, for example oxazolyl, isoxazolyl, oxadiazolyl (e.g. 1,2,4-oxadiazolyl, 1,3,4-oxadiazolyl, 1,2,5-oxadiazolyl, etc.), etc.;

3- through 8-membered saturated monocyclic hetero groups containing 1 or 2 oxygen atoms and 1 to 3 nitrogen atoms, for example morpholinyl, oxazolidinyl (e.g. 1,3-oxazolidinyl etc.), etc.;

unsaturated fused heterocyclic groups containing 1 or 2 oxygen atoms and 1 to 3 nitrogen atoms, for example benzoxazolyl, benzoxadiazolyl, etc.;

3- through 8-membered unsaturated monocyclic hetero groups containing 1 or 2 sulfur atoms and 1 to 3 nitrogen atoms, for example 1,3-thiazolyl, 1,2-thiazolyl, thiazolinyl, thiadiazolyl (e.g. 1,2,4-thiadiazolyl, 1,3,4-thiadiazolyl, 1,2,5-thiadiazolyl, 1,2,3-thiadiazolyl, etc.);

3- through 8-membered saturated monocyclic hetero groups containing 1 or 2 sulfur atoms and 1 to 3 nitrogen atoms, for example thiazolidinyl etc.;

3- through 8-membered unsaturated monocyclic hetero groups containing one sulfur atom, for example thienyl etc.;

unsaturated fused heterocyclic groups containing 1 or 2 sulfur atoms and 1 to 3 nitrogen atoms, for example benzothiazolyl, benzothiadiazolyl, etc.;

3- through 8-membered unsaturated monocyclic hetero groups containing 1 or 2 oxygen atoms, for example furyl, pyranyl, dioxolyl, etc.;

3- through 8-membered saturated monocyclic hetero groups containing 1 or 2 oxygen atoms, for example, oxolanyl, tetrahydropyranyl (e.g. tetrahydro-2H-pyran-2-yl etc.), dioxolanyl, etc.; and unsaturated fused heterocyclic groups containing 1 or 2 oxygen atoms, for example isobenzofuranyl, chromenyl (e.g. 2H-chromen-2-yl etc.), and dihydrochromenyl (e.g. 3,4-dihydro-2H-chromen-4-yl etc.); among others.

The preferred examples of said "heterocyclic group" are 3- through 8-membered unsaturated monocyclic hetero groups containing 1 to 4 nitrogen atoms; 3- through 8-membered saturated monocyclic hetero groups containing 1 to 4 nitrogen atoms; 3- through 8-membered saturated monocyclic hetero groups containing 1 or 2 oxygen atoms and 1 to 3 nitrogen atoms; and 3- through 8-membered saturated monocyclic hetero groups containing 1 or 2 oxygen atoms. The preferred species of those groups include pyridyl, tetrazolyl, piperidyl, piperazinyl, morpholinyl, oxazolidinyl, and tetrahydropyranyl. The still more preferred species are 4-pyridyl, 1H-tetrazol-5-yl, piperidino, 1-piperazinyl, morpholino, 1,3-oxazolidin-5-yl, and tetrahydro-2H-pyran-2-yl.

The "heterocyclic group" mentioned above may have 1 or more (preferably 1 to 3) suitable substituents [for example hydroxy(lower)alkyl (e.g. hydroxymethyl, 2-hydroxyethyl, 1-hydroxypropyl, 4-hydroxybutyl, 2-hydroxy-1,1-dimethylethyl, 3-hydroxypentyl, 6-hydroxyhexyl, etc.), aryl which may have lower alkoxy (e.g. phenyl, naphthyl, 2-methoxyphenyl, 2-methoxynaphthyl, 3-ethoxyphenyl, 4-propoxyphenyl, 2-butoxyphenyl, 5-propoxynaphthyl, 3-t- butoxyphenyl, 4-pentyloxyphenyl, 2-hexyloxyphenyl, etc.), oxo, etc.]. The preferred "suitable substituents" are hydroxy-($C_1$–$C_4$)alkyl, phenyl having ($C_1$–$C_4$)alkoxy, and oxo, with 2-hydroxyethyl, 2-methoxyphenyl, and oxo being particularly preferred.

The preferred species of the "heterocyclic group" of said "heterocyclic group optionally having 1 or more suitable substituents" includes the same specific groups as those mentioned for the "heterocyclic group" of said "lower alkyl having a heterocyclic group which may have 1 or more suitable substituents" and of said "higher alkyl having a heterocyclic group which may have 1 or more suitable substituents". The more preferred are unsaturated fused heterocyclic groups containing 1 or 2 oxygen atoms. The still more preferred is dihydrochromenyl, with 3,4-dihydro-2H-chromen-4-yl being the most preferred.

This "heterocyclic group" may have 1 or more (preferably 1 to 4) suitable substituent groups [for example said lower alkyl, hydroxy, cyano, etc., preferably ($C_1$–$C_4$)alkyl, hydroxy, and cyano, and most preferably methyl, hydroxy, and cyano].

The suitable species of "ar(lower)alkyl" includes mono-, di-, or triphenyl(lower)alkyl (e.g. benzyl, phenethyl, 2-phenylpropyl, 4-phenylbutyl, 2-phenyl-1,1-dimethylethyl, 1-phenylpentyl, 6-phenylhexyl, benzhydryl, trityl, etc.). Among them, the preferred are phenyl($C_1$–$C_4$)alkyl groups and the most preferred is benzyl.

The preferred species of the "nitrogen-containing heterocyclic group" of said "nitrogen-containing heterocyclic group optionally having 1 or more suitable substituents" includes those hetero systems containing at least one nitrogen atom as the ring atom, among the "heterocyclic groups" mentioned hereinbefore, and this "nitrogen-containing heterocyclic group" may have 1 or more (preferably 1 to 3) suitable substituent groups [for example said hydroxy (lower)alkyl, said aryl which may have lower alkoxy, oxo, etc.].

The preferred species of "tetrazolyl(lower)alkyl" includes 1H-tetrazol-5-ylmethyl, 2-(1H-tetrazol-5-yl)ethyl, 3-(1H-tetrazol-5-yl)propyl, 4-(1H-tetrazol-5-yl)butyl, 2-(2H-tetrazol-2-yl)-1,1-dimethylethyl, 4-(1H-tetrazol-1-yl)pentyl, 5-(1H-tetrazol-5-yl)pentyl, 6-(1H-tetrazol-5-yl)hexyl, etc. Among them, the more preferred are tetrazolyl($C_1$–$C_6$)alkyl groups and the still more preferred are (1H-tetrazol-5-yl) methyl, 2-(1H-tetrazol-5-yl)ethyl, 3-(1H-tetrazol-5-yl) propyl, 4-(1H-tetrazol-5-yl)butyl, 5-(1H-tetrazol-5-yl) pentyl, and 6-(1H-tetrazol-5-yl)hexyl.

The preferred species of "tetrazolyl(higher)alkyl" includes 7-(1H-tetrazol-5-yl)heptyl, 8-(1H-tetrazol-5-yl) octyl, 4-(1H-tetrazol-1-yl)octyl, 8-(1H-tetrazol-5-yl)-3-methylheptyl, 9-(1H-tetrazol-5-yl)nonyl, 1-(1H-tetrazol-1-yl)nonyl, 10-(1H-tetrazol-5-yl)decyl, 8-(1H-tetrazol-5-yl) undecyl, 12-(1H-tetrazol-5-yl)dodecyl, 11-(1H-tetrazol-5-yl)-4-methylundecyl, 13-(1H-tetrazol-5-yl)tridecyl, 6-(1H-tetrazol-5-yl)tetradecyl, 15-(1H-tetrazol-5-yl)pentadecyl, 12-(1H-tetrazol-5-yl)hexadecyl, 17-(1H-tetrazol-1-yl) heptadecyl, 4-(1H-tetrazol-5-yl)octadecyl, 19-(1H-tetrazol-5-yl)nonadecyl, 1-(1H-tetrazol-1-yl)-12-ethylheptadecyl, 20-(1H-tetrazol-5-yl)eicosyl, etc. Among them, the more preferred are tetrazolyl($C_7$–$C_{16}$)alkyl groups and the still more preferred are 7-(1H-tetrazol-5-yl)heptyl, 8-(1H-tetrazol-5-yl)-octyl, 9-(1H-tetrazol-5-yl)nonyl, 10-(1H-tetrazol-5-yl)decyl, and 12-(1H-tetrazol-5-yl)dodecyl.

The preferred "cyclo(lower)alkyl" is cyclo($C_3$–$C_8$)alkyl, for example cyclopropyl, cyclobutyl, cyclopentyl, cyclohexyl, cycloheptyl, and cyclooctyl, with cyclo($C_5$–$C_7$) alkyl groups such as cyclopentyl, cyclohexyl, and cycloheptyl being particularly preferred.

This "cyclo(lower)alkyl" may have 1 or more (preferably 1~3) suitable substituent groups selected from the class consisting of acyl(lower)alkyl, acyl(lower)alkylidene, etc.

The preferred species of "cyclo(lower)alkenyl" includes cyclo($C_3$–$C_8$)alkenyl groups such as cyclopropenyl, cyclobutenyl, cyclopentenyl, cyclohexenyl, cycloheptenyl, and cyclooctenyl. Among them, the more preferred are cyclo ($C_5$–$C_7$) alkenyl groups such as cyclopentenyl, cyclohexenyl, cycloheptenyl, etc. and the still more preferred is cyclohexenyl or cycloheptenyl.

The "cyclo(lower)alkenyl" mentioned above may have 1 or more (preferably 1~3) suitable substituent groups such as those mentioned above for "cyclo(lower)alkyl".

The preferred species of said "acyl(lower)alkyl" includes carboxy(lower)alkyl groups, for example carboxymethyl, 2-carboxyethyl, 3-carboxypropyl, 1-carboxymethylethyl, 4-carboxybutyl, 2-carboxymethyl-2-methylethyl, 5-carboxypentyl, 3-carboxyhexyl, etc. and lower alkanoyl (lower)alkyl groups, for example acetylmethyl, formylmethyl, 2-acetylethyl, 2-propionylpropyl, 4-butyrylbutyl, 3-pentanoylpentyl, 6-hexanoylhexyl, etc. Among those groups, carboxy($C_1$–$C_4$)alkyl and ($C_1$–$C_4$) alkanoyl($C_1$–$C_4$)alkyl are preferred. The still more preferred is carboxymethyl, 2-carboxyethyl, 3-carboxypropyl, or acetylmethyl.

Among other preferred examples of "acyl(lower)alkyl" are protected carboxy (lower) alkyl groups, and the more preferred among them are esterified carboxy(lower)alkyl groups. The still more preferred are lower alkoxycarbonyl (lower)alkyl groups such as methoxycarbonylmethyl, ethoxycarbonylmethyl, 2-ethoxycarbonylethyl, 1-propoxycarbonylpropyl, 2-isopropoxycarbonylpropyl, butoxycarbonylmethyl, t-butoxycarbonylmethyl, 4-isobutoxycarbonylbutyl, 3-pentyloxycarbonylpentyl, 6-hexyloxycarbonylhexyl, (1-cyclopropylethoxycarbonyl) methyl, etc. and phenyl(lower)alkoxycarbonyl(lower)alkyl groups such as benzyloxycarbonylmethyl, 2-benzyloxycarbonylethyl, 1-phenethyloxycarbonylethyl, 3-benzyloxycarbonylpropyl, 2-benzyloxycarbonylbutyl, 2-phenethyloxycarbonylmethyl-2-methylethyl, 3-benzyloxycarbonylpentyl, 6-benzyloxycarbonylhexyl, etc. The still more preferred are ($C_1$–$C_4$)alkoxycarbonyl ($C_1$–$C_4$)alkyl and phenyl($C_1$–$C_4$)alkoxycarbonyl($C_1$–$C_4$) alkyl groups and the particularly preferred species are methoxycarbonylmethyl, ethoxycarbonylmethyl, t-butoxycarbonylmethyl, 2-benzyloxycarbonylethyl, and 3-benzyloxycarbonylpropyl.

The preferred species of "acyl (lower) alkylidene" includes carboxy(lower)alkylidene groups such as carboxymethylene, 2-carboxyethylidene, 2-carboxypropylidene, 4-carboxybutylidene, 5-carboxypentylidene, 3-carboxyhexylidene, etc. The more preferred, among them, are carboxy ($C_1$–$C_4$) alkylidene groups and the most preferred is carboxymethylene.

As other preferred examples of "acyl(lower)alkylidene", there can be mentioned protected carboxy(lower)alkylidene groups. The preferred are esterified carboxy(lower) alkylidene groups and the still more preferred are lower alkoxycarbonyl(lower)alkylidene groups such as methoxycarbonylmethylene, ethoxycarbonylmethylene, 2-ethoxycarbonylethylidene, 1-propoxycarbonylpropylidene, 2-isopropoxycarbonylpropylidene, butoxycarbonylmethylene, t-butoxycarbonylmethylene, 4-isobutoxycarbonylbutylidene, 3-pentyloxycarbonylpentylidene, 6-hexyloxycarbonylhexylidene, (1-cyclopropylethoxycarbonyl)methylene, etc. The still more preferred are $(C_1-C_4)$alkoxycarbonyl$(C_1-C_4)$ alkylidene groups, with methoxycarbonylmethylene, ethoxycarbonylmethylene, and t-butoxycarbonylmethylene being particularly preferred.

Referring to the pyrazolopyridine compound (I) described above, the following specific compounds can be mentioned as the particularly preferred compounds for the practice of the present invention.
(1) (2R)-1-[3-(2-Phenylpyrazolo[1,5-a]pyridin-3-yl) acryloyl]-2-(2-hydroxyethyl)piperidine (trans isomer)
(2) 3-[2-(3-Carboxypropyl)-3-oxo-2,3-dihydropyridazin-6-yl]-2-phenylpyrazolo[1,5-a]pyridine
(3) (2R)-1-[3-(2-Phenylpyrazolo[1,5-a]pyridin-3-yl) acryloyl]-2-(carboxymethyl)piperidine (trans isomer)
(4) 3-[2-(2-Carboxymethyl-1-cyclohexenyl)-3-oxo-2,3-dihydropyridazin-6-yl]-2-phenylpyrazolo[1,5-a]pyridine Referring to the pharmaceutical composition for use in reducing the invention to practice, the pyrazolopyridine compound (I) or its salt can be used as it is or in the form of a solid, semi-solid or liquid dosage form containing it as an active ingredient as formulated with an organic or inorganic carrier or excipient suitable for rectal, oral or parenteral (inclusive of subcutaneous, intravenous and intramuscular) administration or for inhalation. The active ingredient can be formulated with conventional non-toxic, pharmaceutically acceptable carriers which are generally used in the manufacture of tablets, pellets, troches, capsules, suppositories, aerosols, powders for inhalation, solutions, emulsions, suspensions and other suitable dosage forms. Where necessary, an adjuvant, stabilizer, thickener, coloring agent, and perfume can be added. The pyrazolopyridine compound (I) or its salt can be present in such a pharmaceutical composition in an amount sufficient to achieve the desired prophylactic or therapeutic result according to the course or stage of illness.

The pharmaceutical composition or dosage form can be manufactured by the routine technology in the field of art. Where necessary, the various contrivances for enhancing the bioavailability of drugs, which are known to those skilled in the art, can be utilized in the manufacture of the pharmaceutical composition.

For application of composition of the invention to man or animals, the preferred route of administration is intravenous administration (inclusive of its addition to drip infusions), intramuscular administration, or oral administration.

The prophylactically and/or therapeutically effective amount of pyrazolopyridine compound (I) varies with the patient or animal's age and other conditions. However, for the therapy and/or prevention of ischemic intestinal lesions and/or ileus, the pyrazolopyridine compound (I) can be generally administered to man or an animal intravenously in a daily dose of 0.01~100 mg per kg body weight, intramuscularly in a daily dose of 0.01–100 mg per kg body weight, or orally in a daily dose of 0.01–200 mg per kg body weight.

The pharmaceutical composition of the invention is useful for the prevention and/or treatment of ischemic intestinal lesions and/or ileus.

The term "ischemic intestinal lesions" is used herein to mean any and all of acute intestinal insufficiency (e.g. acute mesenteric vessel occlusion, acute hemorrhagic intestinal necrosis, etc.), chronic intestinal insufficiency (e.g. intestinal angina, intestinal luminal artery compression syndrome, etc.) ischemic enteritis (e.g. ischemic colitis, ischemic inflammation of the small intestine, occlusive colitis, post-traumatic ischemic stenosis, post-vascular surgery ischemic enteritis, drug-induced ischemic enteritis, etc.), ischemic bowel lesions associated with phlebosclerosis, amyloidosis, collagen disease, radiation enteritis, Schoenlein-Henock purpura, stercoral ulcer and acute hemorrhagic rectal ulcer, among other diseases.

The "ileus" is used herein to mean any and all of mechanical ileus (ileus simplex, strangulated ileus, etc.) and functional ileus [paralytic ileus (postoperative ileus etc.),spastic ileus, etc.], among others.

For demonstrating the usefulness of the present invention, the results of pharmacological tests performed using the pharmaceutical composition of the invention are shown below.

I. Test 1
1. Test preparations
Preparation (1):
   3-[2-(3-Carboxypropyl)-3-oxo-2,3-dihydropyridazin-6-yl]-2-phenylpyrazolo[1,5-a]-pyridine suspended in 0.5% methylcellulose
Preparation (2):
(2R)-1-[3-(2-Phenylpyrazolo[1,5-a]pyridin-3-yl)acryloyl]-2-(carboxymethyl)piperidine (trans isomer) dissolved in equimolar NaOH solution
2. Test method Male SD rats (230~260 g) were anesthetized with pentobarbital (50 mg/kg, i.p.). After 30 minutes, the abdomen was opened to expose the descending colon and the marginal artery and vein were clipped with arterial clips at intervals of about 2 cm for 30 minutes. Thirty (30) minutes after unclipping, carmine (a nonabsorbable marker) was administered from a cannula indwelt in the proximal colon 5 days before and the colonic transport rate (%; distance of transport of carmine/total length of colon) after 5 hours was determined.

In the evaluation of prophylactic efficacy, the above preparation (1) (1 mg/kg) was administered orally 30 minutes before pentobarbital dosing. In the evaluation of therapeutic efficacy, the above preparation (2) (1 mg/kg) was administered intravenously 1 and 3 hours after unclipping.
3. Test results The action (prophylactic effect) of preparation (1) on colonic transport failure caused by ischemia-reperfusion

|  | Sham operation group | Control group (ischemia and reperfusion) | Preparation (1) treatment group (1 mg/kg) |
| --- | --- | --- | --- |
| n | 5 | 8 | 8 |
| Colonic transport (%) | 89.6 ± 6.6 | 61.5 ± 8.4 | 96.6 ± 3.4* |

*: $P < 0.01$ vs. control

The action (therapeutic effect) of preparation (2) on colonic transport failure caused by ischemia-reperfusion

|  | Sham operation group | Control group (ischemia and reperfusion) | Preparation (1) treatment group (1 mg/kg) Administered 1 hr after reperfusion | Preparation (2) treatment group (1 mg/kg) Administered 3 hr after reperfusion |
| --- | --- | --- | --- | --- |
| n | 8 | 10 | 7 | 10 |
| Colonic transport (%) | 68.9 ± 4.7 | 61.7 ± 7.2 | 100 ± 0.0* | 92.4 ± 4.3* |

*: $P < 0.01$ vs. control

II. Test 2
1. Test preparation
The preparation (2) used in Test 1 (concentrations: 0.1 mg/kg and 1.0 mg/kg) was used.

2. Test method

Male SD rats were used. To construct a postoperative ileus model, one-half of the stomach was excised off on the day preceding the determination of colonic transport rate. At the same time, a cannula for determination of colonic transport rate was inserted in the proximal colon of hemi-gastrectomized rats and normal rats and extracorporeally exposed from the occipital region. The non-absorbable marker carmine was administered from the cannula and the 2-hour colonic transport rate (%; distance of transport of carmine/length of the whole colon) was determined. Preparation (2) was administered from the caudal vein at the same time as administration of carmine.

3. Test results

The action of preparation (2) on the post-hemigastrectomy ileus model

|  | Colonic transport rate (%) |
|---|---|
| Normal group | 88.60 ± 3.85** |
| Hemi-gastrectomized model, control group | 63.92 ± 6.07 |
| Preparation (2) treatment group, 0.1 mg/kg | 80.01 ± 5.66 |
| Preparation (2) treatment group, 1.0 mg/kg | 89.90 ± 3.79** |

**$P < 0.01$ vs. control group

Gastrectomy caused a motility inhibition of about 28%. In this model, preparation (2) showed dose-dependent curative efficacy, with complete recovery to normal motility at 1.0 mg/kg.

III. Test 3

1. Test preparation

The preparation (2) used in Test 1 (concentrations: 0.1 mg/kg and 1.0 mg/kg) was used.

2. Test method

Male SD rats were used. One hour after administration of pentobarbital (50 mg/kg, i.v.), preparation (2) and carmine were administered and the 2-hour colonic transport rate was determined in the same manner as above.

3. Test results

The action of preparation (2) on the anesthesia-induced ileus model

|  | Colonic transport rate (%) |
|---|---|
| Normal group | 86.33 ± 3.21** |
| Anesthesia-induced ileus model, control group | 55.99 ± 2.43 |
| Preparation (2) treatment group, 0.1 mg/kg | 76.51 ± 6.56** |
| Preparation (2) treatment group, 1.0 mg/kg | 90.27 ± 3.84** |

**$P < 0.01$ vs. control group

Pentobarbital dosing resulted in a motility inhibition of about 35%. In this model, preparation (2) showed dose-dependent prokinetic efficacy, with complete recovery to normal motility at 1.0 mg/kg.

It is evident from the above test results that the pharmaceutical composition of the present invention effectively prevents gastrointestinal dysfunction and effectively ameliorates pre-induced gastrointestinal dysfunction.

It is, therefore, clear that the present invention is effective in the prophylaxis and therapy of ischemic intestinal lesions and/or ileus.

What is claimed is:

1. A method of treating and/or preventing ischemic intestinal lesions and/or ileus in a patient comprising administering to the patient an ischemic intestinal lesions and/or ileus-therapeutically and/or prophylactically effective amount of a pyrazolopyridine compound of the following general formula:

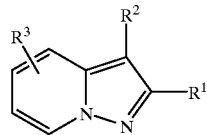

wherein $R^1$ is lower alkyl, aryl which may have one or more suitable substituent(s), or heterocyclic group;

$R^2$ is a group of the formula:

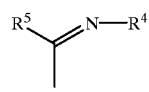

(wherein $R^4$ is protected amino or hydroxy and $R^5$ is hydrogen or lower alkyl), cyano, a group of the formula: —A—$R^6$ (wherein $R^6$ is acyl and A is a lower aliphatic hydrocarbon group which may have one or more suitable substituent(s)), amidated carboxy, unsaturated heterocyclic group which may have one or more suitable substituent(s), amino, or protected amino; and $R^3$ is hydrogen, lower alkyl, lower alkoxy, or halogen;

or a salt thereof.

2. The method according to claim 1 wherein the pyrazolopyridine compound is a compound of the general formula:

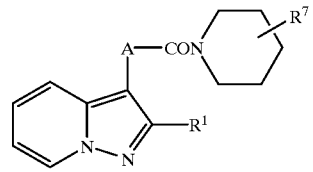

(wherein $R^1$ is aryl;

$R^7$ is acyl(lower)alkyl or hydroxy(lower)alkyl; and

A is lower alkenyl).

3. The method according to claim 2 wherein the pyrazolopyridine compound is the compound of claim 2 wherein $R^1$ is phenyl and $R^7$ is carboxy(lower)alkyl.

4. The method according to claim 3 wherein the pyrazolopyridine compound is 1-[3-(2-phenylpyrazolo[1,5-a]pyridin-3-yl)acryloyl]-2-(carboxymethyl)piperidine.

5. The method according to claim 1 wherein the pyrazolopyridine compound is a compound of the general formula:

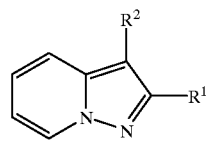

wherein $R^1$ is aryl and $R^2$ is dihydropyridazinyl having acyl(lower)alkyl and oxo; dihydropyridazinyl having acyl (lower)alkyl- or acyl(lower)alkylidene-substituted cyclo(lower)alkyl and oxo; or dihydropyridazinyl having acyl(lower)alkyl- or acyl(lower)alkylidene-substituted cyclo(lower)alkenyl and oxo.

6. The method according to claim 5 wherein the pyrazolopyridine compound is the compound of claim 5 wherein $R^1$ is phenyl and $R^2$ is 3-oxo-2,3-dihydropyridazinyl having carboxy(lower)alkyl or 3-oxo-2,3-dihydropyridazinyl having carboxy(lower)alkyl-substituted cyclo(lower)alkenyl.

7. The method according to claim 6 wherein the pyrazolopyridine compound is 3-[2-(3-carboxypropyl)-3-oxo-2,3-dihydropyridazin-6-yl]-2-phenylpyrazolo[1,5-a]pyridine.

8. The method according to claim 6 wherein the pyrazolopyridine compound is 3-[2-(2-carboxymethyl-1-cyclohexenyl)-3—oxo-2,3-dihydropyridazin-6-yl]-2-phenylpyrazolo[1,5-a]pyridine.

* * * * *

UNITED STATES PATENT AND TRADEMARK OFFICE
CERTIFICATE OF CORRECTION

PATENT NO. : 6,214,843 B1          Page 1 of 1
DATED : April 10, 2001
INVENTOR(S) : Kadowaki et al.

It is certified that error appears in the above-identified patent and that said Letters Patent is hereby corrected as shown below:

Title page,
Item [73], should read as follows:

Assignee: Fujisawa Pharmaceutical Co., Ltd.,
          Osaka [JP]

Signed and Sealed this

Twentieth Day of November, 2001

Attest:

*Nicholas P. Godici*

NICHOLAS P. GODICI
*Attesting Officer*     *Acting Director of the United States Patent and Trademark Office*